US00PP30278P2

(12) United States Plant Patent
Danziger

(10) Patent No.: US PP30,278 P2
(45) Date of Patent: Mar. 5, 2019

(54) ***SCAEVOLA* PLANT NAMED 'DSCAVPIBLS'**

(50) Latin Name: *Scaevola aemula*
Varietal Denomination: DSCAVPIBLS

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 15/732,534

(22) Filed: Nov. 27, 2017

(51) Int. Cl.
*A01H 5/02* (2018.01)

(52) U.S. Cl.
USPC ..... Plt./363

(58) Field of Classification Search
USPC ..... Plt./363
See application file for complete search history.

*Primary Examiner* — Susan McCormick Ewoldt
(74) *Attorney, Agent, or Firm* — Cassandra Bright

(57) ABSTRACT

A new and distinct *Scaevola* cultivar named 'DSCAVPIBLS' is disclosed, characterized by a strong pink flower color with a dark pink eye. The plant has a strong, sturdy foliage and a unique semi-trailing habit. The variety is characterized by early and abundant flowering. The new variety is a *Scaevola*, normally produced as an outdoor garden or container plant.

2 Drawing Sheets

Figure 1:
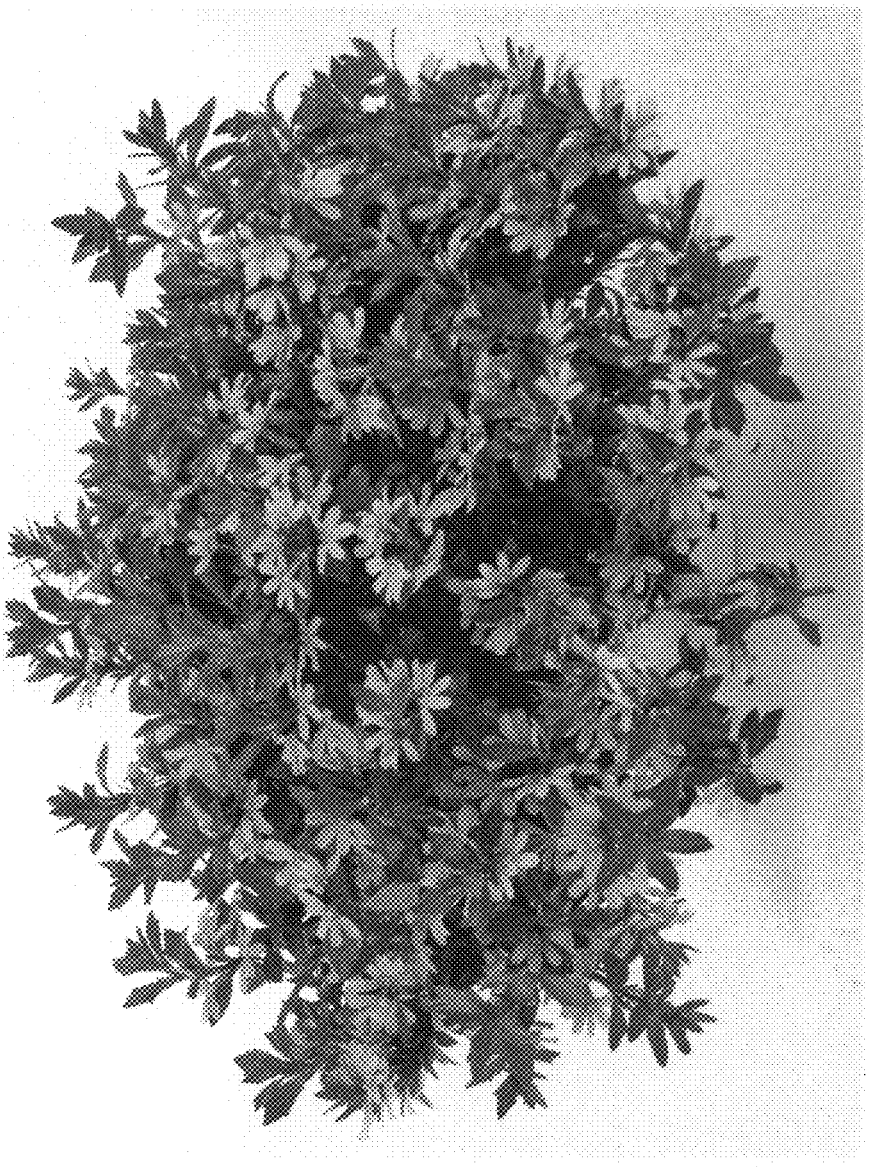

Latin name of the genus and species: *Scaevola aemula.*
Variety denomination: 'DSCAVPIBLS'.

BACKGROUND OF THE INVENTION

The new *Scaevola* cultivar is the product of a planned breeding program conducted by the inventor, Gavriel Danziger, in Moshav Mishmar Hashiva, Israel. The objective of the breeding program was to produce new *Scaevola* varieties with denser plant habits, strong garden performance, in a range of flower colors. The cross resulting in this new variety was made in 2014.

le;.5qThe seed parent is the unpatented *Scaevola* 'DSCAVPICHA'. The pollen parent is the unpatented, proprietary variety *Scaevola* 'cv. 11-769'. The new variety was identified as a potentially interesting selection in December 2014, at a research greenhouse in Moshav Mishmar Hashiva, Israel.

Asexual reproduction of the new cultivar 'DSCAVPIBLS' by vegetative cuttings was first performed during 2014, at a research greenhouse in Moshav Mishmar Hashiva, Israel. Subsequent propagation has shown that the unique features of this cultivar are stable and reproduced true to type on successive generations.

SUMMARY OF THE INVENTION

The cultivar 'DSCAVPIBLS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DSCAVPIBLS' These characteristics in combination distinguish 'DSCAVPIBLS' as a new and distinct *Scaevola* cultivar:

1. Strong pink color with dark pink eye.
2. Semi-trailing habit.
3. Floriferous plants.
4. Foliage tolerant to cold temperatures.

PARENT COMPARISON

Plants of the new cultivar 'DSCAVPIBLS' are similar to plants of the seed parent in most horticultural characteristics, however, plants of the new cultivar 'DSCAVPIBLS' differ in the following;

1. 'DSCAVPIBLS' has better overall and garden performance, less leggy and more tolerant of environmental stressors.
2. 'DSCAVPIBLS' is more vigorous than 'DSCAVPICHA'.
3. 'DSCAVPIBLS' has larger flowers and long flowering stems than 'DSCAVPICHA'.

Plants of the new cultivar 'DSCAVPIBLS' are similar to plants of the pollen parent, 'cv. 11-769' in most horticultural characteristics, however, plants of the new cultivar 'DSCAVPIBLS' differ in the following;

1. Flowers of 'DSCAVPIBLS' are pink, flowers of 'cv.11-769' are purple.
2. 'DSCAVPIBLS' flowers earlier than 'cv.11-769'.

COMMERCIAL COMPARISON

Plants of the new cultivar can be compared to the unpatented commercial variety 'Topaz Pink'. These varieties are similar in most horticultural characteristics; however, 'DSCAVPIBLS' differs in the following:

1. 'DSCAVPIBLS' is more vigorous than 'Topaz Pink'.
2. 'DSCAVPIBLS' flower color is darker than 'Topaz Pink' flowers.
3. 'DSCAVPIBLS' has better overall and garden performance.

Plants of the new cultivar can also be compared to the commercial variety 'DSCAVPUHAZ', U.S. U.S. Plant Pat. No. 29,544. These varieties are similar in most horticultural characteristics; however, 'DSCAVPIBLS' differs in the following:

1. Plants of 'DSCAVPIBLS' are more vigorous than plants of 'DSCAVPUHAZ'.

2. Flowers of 'DSCAVPIBLS' are pink, flowers of 'DSCAVPUHAZ' are purple.
3. 'DSCAVPIBLS' has a different more semi trailing plant habit, plants of 'DSCAVPUHAZ' are more upright.

BRIEF DESCRIPTION OF THE PHOTOGRAPHS

The accompanying photograph in FIG. 1 illustrates in full color a typical plant of 'DSCAVPIBLS' grown in a greenhouse, in Moshav Mishmar Hashiva, in a 15 cm pot.

Figure 2:
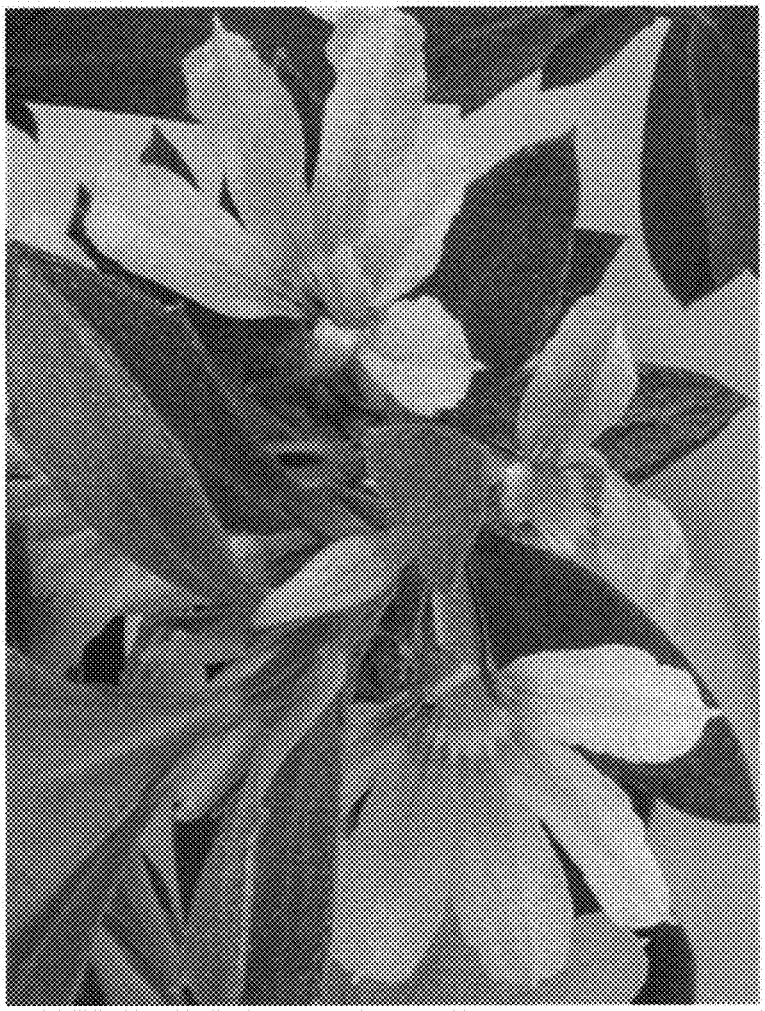

FIG. 2 illustrates in full color a close-up view of typical flowers of 'DSCAVPIBLS'. Age of the plant photographed is approximately 6 months from an unrooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Mini Chart, 2015 except where general terms of ordinary dictionary significance are used. The following observations and measurements describe 'DSCAVPIBLS' plants grown in a greenhouse in Moshav Mishmar Hashiva. The growing temperature ranged from 15° C. to 28° C. during the day and 10° C. to 15° C. at night. The greenhouse is un-shaded, giving bright, normal sunlight conditions. Measurements and numerical values represent averages of typical plant types.

Botanical classification: *Scaevola aemula* 'DSCAVPIBLS'.

PROPAGATION

Time to initiate roots: About 16-21 days at approximately 18° C.

Root description: Fibrous. White and tan, not accurately measured with an R.H.S. chart.

Time to produce a rooted cutting: About 30 days at 18° C.

PLANT

Growth habit: Semi-trailing flowering annual.
Age of plant described: 3 months.
Container size: 20 cm basket.
Height: 19 cm.
Plant spread: 30-35 cm.
Quantity of lateral branches: 30.
Lateral branch description:
- *Diameter*.—Approximately 0.4 mm.
- *Length*.—30 cm.
- *Texture*.—Smooth.
- *Color*.—146A.

Internode length: Average 2 cm.

FOLIAGE

Leaf:
- *Arrangement*.—Alternate.
- *Quantity*.—Approximately 15-20 fully expanded per main branch.
- *Average length*.—Approximately 5-6 cm.
- *Average width*.—Approximately 2 cm.
- *Shape of blade*.—Oblong and runcinate.
- *Apex*.—Blunt and dentate.
- *Base*.—Cuneate.
- *Attachment*.—Sessile.
- *Margin*.—Dentate.
- *Texture of top surface*.—Rough.
- *Texture of bottom surface*.—Rough.
- *Color*.—Young foliage upper side: Near Green 137B RHS. Young foliage under side: Near Yellow-Green 144A RHS. Mature foliage upper side: Near Green 137A RHS. Mature foliage under side: Near Green 138B RHS.
- *Venation*.—Type: Pinnate. Only midrib and 2 secondary veins visible. Venation color upper side: Near Green 137A RHS. Venation color under side: Near Green 138B RHS.
- *Petiole*.—Length: 1.5 cm. Width: 0.5 cm. Color: Near Yellow-Green 146C RHS. Texture: Glabrous.

FLOWER

Natural flowering season: Spring, Summer and Autumn continuously in Beit Dagan Israel.
Inflorescence type and habit: Flowers single occurring from leaf axils. Clustered at terminus.
Flower longevity on plant: About 20 days.
Quantity of flowers: About 200-250 per plant.
Individual flowers:
Size:
- *Diameter*.—Approximately 3 cm.
- *Length*.—Approximately 3 cm.
- *Persistence*.—Non-persistent.
- *Fragrance*.—None.

Corolla:
- *Petal arrangement*.—5 petals, fused from base, to approximately 50% of length, forming a half tube. Separated portion radiating into a semi-circle/fan shape.
- *Margin*.—Entire.
- *Apex*.—Abruptly acute.
- *Shape*.—Oblong.
- *Length*.—1.5-2.5 cm. Unfused portion: 1.3-1.5 cm. Half Tube: 1 cm.
- *Width*.—Unfused portion: 0.6 cm. Half Tube: 0.4 cm.
- *Texture*.—Velvety.

Color:
- *Separate petals*.—When opening: Upper surface: Red 54C with Red-Purple N74A eye. Lower surface: Red 54D. Fully opened: Upper surface: Red 54C with Red-Purple N74B eye. Lower surface: Red 54D. Fading: Upper surface: Red 54D. Lower surface: Red 54D.

Color:
- *Half-tube*.—When opening: Upper surface: Green-Yellow 1A. Lower surface: Green-Yellow 1D. Fully opened: Upper surface: Green-Yellow 1B. Lower surface: Green-Yellow 1D. Fading: Upper surface: Green-Yellow 1B. Lower surface: Green-Yellow 1D.

Bud:
- *Shape*.—Fusiform.
- *Length*.—Approximately 1.5 cm.
- *Diameter*.—Approximately 0.3 cm.
- *Color*.—Near Green-Yellow 1C RHS.

Calyx:
- *Length*.—Approximately 0.3 cm.
- *Diameter*.—Approximately 0.2 cm.

Sepals:
*Quantity.*—2.
*Shape.*—Ligulate.
*Length.*—1 cm.
*Width.*—2 mm.
*Margin.*—Entire.
*Apex.*—Acute.
*Texture.*—Rough. Color: Mature: Yellow-Green 146A RHS.

Pedicel:
*Length.*—Average 0.2 cm.
*Diameter.*—0.1 cm.
*Color.*—Near Green 143C RHS.
*Orientation.*—Approximately 45° angle from attachment.
*Strength.*—Good.
*Texture.*—Glabrous.

Fragrance: None.

REPRODUCTIVE ORGANS

Stamens:
*Number.*—5.
*Filament length.*—Approximately 0.4 cm.
*Filament color.*—Near Green-Yellow 1D RHS.

Anthers:
*Shape.*—Ligulate.
*Length.*—Approximately 0.5 mm.
*Color.*—Near Green-Yellow 1D.
*Pollen.*—Small amount, colored Yellow 9D.

Pistil:
*Number.*—1.
*Length.*—Approximately 1.4 cm.
*Style.*—Length: Approximately 1.0 cm. Color: Near Red-Purple 59A.
*Stigma.*—Shape: Oblate. Texture: Hairy, pilose. Color: Red-Purple 59B with Yellow 2D tip. Ovary color: Green 143C.

OTHER CHARACTERISTICS

Seeds and fruits: One ellipsoid black seed 2 mm diameter 4 mm long per flower. Colored near Black 202A.

Disease/pest resistance: Neither resistance nor susceptibility to normal diseases and pests of *Scaevola* has been observed.

Temperature tolerance: Temperature range: Observed to tolerate temperatures from 5° C. to at 45° C.

What is claimed is:

1. A new and distinct cultivar of *Scaevola* plant named 'DSCAVPIBLS' as herein illustrated and described.

* * * * *